United States Patent [19]
Holmgren et al.

[11] Patent Number: 5,681,571
[45] Date of Patent: Oct. 28, 1997

[54] IMMUNOLOGICAL TOLERANCE-INDUCING AGENT

[75] Inventors: Jan Holmgren, Västra Frölunda; Cecil Czerkinsky, Göteborg, both of Sweden

[73] Assignee: Duotol AB, Västra Frölunda, Sweden

[21] Appl. No.: 184,458

[22] Filed: Jan. 19, 1994

Related U.S. Application Data

[63] Continuation-in-part of Ser. No. 160,106, Nov. 30, 1993, abandoned.

[30] Foreign Application Priority Data

Oct. 8, 1993 [SE] Sweden ................................ 9303301

[51] Int. Cl.$^6$ ................ A61K 39/02; A61K 39/108; A61K 39/106
[52] U.S. Cl. ................ 424/236.1; 424/241.1; 424/275.1; 424/282.1; 424/810; 514/885; 530/868
[58] Field of Search ............. 424/282.1, 810, 424/275.1, 241.1, 236.1; 514/885; 530/868

[56] References Cited

FOREIGN PATENT DOCUMENTS 8606635 11/1986 WIPO.

OTHER PUBLICATIONS

Theof.lopoulos A.N. "Autoimmunity" in *Basic & Clinical Immunology* 6th ed. Stites et al eds, Appleton & Lange, Norwalk CT. 1987, pp. 128–158.
Ernst et al, "Immunity in Mucusal Tissues" in *Basic & Clinical Immunology* 6th ed. Stites et al eds, Appleton & Lange, Norwalk CT. 1987, pp. 159–166.
Dertzbaugh et al, Infect. Immun 61(2):384–390, 1993.
Bianchi et al Reg. Immunology 3(3):131–138, 1990.
Raine CS. "Experimental allergic encephalomyelitis and experimental allergic neuritis" in *Handbook of Clinical Neurology* vol. 3(47) *Demylenating Diseases* Koetsier et al eds. Elsevier Science Publishers, 1985 pp. 429–466.
Alvord et al, Annals of Neurology 6(6): 461–468, 1979.
Ruitt et al *Immunology* Gowen Medical Publishing London 1985 p. 19.1.
Weiner, H.L., *Treatment of Autoimunune Diseases By Oral Tolerance, Mucosal Immunology Update* (Fall, 1993), pp. 1–16.
Weiner, H.L., Friedman, A., Miller, A. Khoury, S.J., Al–Sabbagh, A., Santos, L., Sayegh, M., Nussenblatt, R.B., Trentham, D.E., Hafler, D.A., *Oral Tolerance: Immunologic mechanisms and treatment of murine and human organ specific autoimmune diseases by oral administration of autoantigens*, Ann. Rev. Immunol., OT Rev. Aug. 17, 1993, 3:53 PM, pp. 1–45, 3 sheet of Figures (FIGS. 1–3).
Mcl. Mowat, A., *The regulation of immune responses to dietary protein antigens*, Immunology Today, vol. 8, No. 3, 1987, pp. 93–98.
Thompson, H.S.G. and Staines, N.A., *Could specific and tolerance be a therapy for autoimmune disease?*, Immunology Today, vol. 11, No. 11, 1990, pp. 396–399.

Czerkinsky, C., Russell, M.W., Lycke, N., Lindblad, M., and Holmgren, J., *Oral Administration of a Streptococcal Antigen Coupled to Cholera Toxin B Subunit Evokes Strong Antibody Responses in Salivary Glands and Extramucosal Tissues, Infection and Immunity*, vol. 57, No. 4, Apr. 1989, pp. 1072–1077.
DeAizpurua, H.J., and Russell–Jones, G.J., *Oral Vaccination: Identification of Classes of Proteins that Provoke an Immune Response upon Oral Feeding, From the Immunochemistry Laboratory, Biotechnology Australia Pty. Ltd., Sydney, Australia*, J. Exp. Med., The Rockefeller University Press, vol. 167, Feb. 1988, pp. 440–451.1.
Vives, J., Parks, D.E., and Weigle, W.O., *Immunologic Unresponsiveness After Gastric Administration of Human γ-Globulin: Antigen Requirements and Cellular Parameters, From the Department of Immunopathology, Scripps Clinic and research Foundation, La Jolla, CA*, The Journal of Immunology, vol. 125, No. 4, Oct. 1980, pp. 1811–1816.
Zhang, Z.J., Lee, C.S.Y., Lider, O., and Weiner, H.L., *Suppression Of Adjuvant Arthritis In Lewis Rats By Oral Administration Of Type II Collagen, From the Center for Neurologic Diseases, Division of Neurology, Department of Medicine, Brigham & Women's Hospital, Harvard Medical School, Boston, MA 02115*, The Journal of Immunology, vol. 145, No. 8, Oct. 15, 1990, pp. 2489–2493.
Nedrud, J.G., Liang, X., Hague, N., and Lamm, M.E., *Combined Oral/Nasal Immunication Protects Mice From Sendai Virus Infection, From the Institute of Pathology, Case Western Reserve University, Cleveland, OH 44106*, The Journal of Immunology, vol. 139, No. 10, Nov. 15, 1987, pp. 3484–3492.
McKenzie, S.J., and Halsey, J.F., *Cholera Toxin B Subunit As A Carrier Protein To Stimulate A Mucosal Immune Response, From the Department of Biochemistry, University of Kansas College of Health Sciences and Hospital, Kansas City, KS 66103*, The Journal of Immunology, vol. 133, No. 4, Oct. 1984, pp. 1818–1824.
Elson, C.O., and Ealding, W., *Cholera Toxin Feeding Did OT Induce Oral Tolerance In Mice And Abrogated Oral Tolerance To An Unrelated Protein Antigen, From the Department of Medicine, Medical College of Virginia, Virginia Commonwealth University, Richmond VA*, The Journal of Immunology, vol. 133, No. 6, Dec. 1984, pp. 2892–2897.
Elson et al, J. Immunol 133(6):2892–2897, 1984.
Clements et al, Vaccine 6:269–277, 1988.
Romaghahi et al, Int. Arch. Allergy Immunol 98:279–285 1992.
Spangler–BD, Microbiological Reviews, 56(4): 622–647, 1992.
Sell S. *Immunology Immunopathology & Immunity* 4th ed. Elsevier, N.Y. 1987 pp. 272–274 & 285–293.

*Primary Examiner*—James C. Housel
*Assistant Examiner*—Rodney P. Swartz
*Attorney, Agent, or Firm*—Darby & Darby

[57] ABSTRACT

An immunological tolerance-inducing agent comprising a mucosa-binding molecule linked to a specific tolerogen is disclosed. Further, a method of inducing immunological tolerance in an individual against a specific antigen, including hapten, which causes an unwanted immune response in said individual comprising administration by a mucosal route of an immunologically effective amount of an immunological tolerance-inducing agent of the invention to said individual, is described.

27 Claims, No Drawings

IMMUNOLOGICAL TOLERANCE-INDUCING AGENT

This is a continuation-in-part of application Ser. No. 08/160,106, filed Nov. 30, 1993, now abandoned.

The present invention relates to an immunological tolerance-inducing agent. Specifically it relates to such an agent comprising a mucosa-binding molecule linked to a specific tolerogen and to a method of inducing immunological tolerance in an individual against a specific antigen, including hapten.

BACKGROUND OF THE INVENTION AND DISCUSSION OF PRIOR ART

Introduction of a foreign substance, in the following referred to as antigen (Ag), including hapten, by injection into a vertebrate organism may result in the induction of an immune response characterized by the production of specific antibodies (products of B lymphocytes) capable of interacting with said Ag and/or the development of effector T lymphocytes and the production of soluble mediators, termed lymphokines, at the site of encounter with said Ag. Antibodies and T lymphocytes do certainly play an essential role in protecting against hostile Ag but can also participate in injurious processes leading to destruction of host tissues. This is the case in autoimmune diseases where antibodies and/or T lymphocytes react with Ag of one's own tissues and damage these. This is also the case in allergic reactions characterized by an exaggerated immune response to certain environmental matters and which may result in inflammatory responses leading to tissue destruction. Moreover, this is the case in chronic inflammatory reactions that develop as a result of ineffective elimination of foreign materials as in certain infections (e.g. tuberculosis, schisto-somiasis) or following introduction of foreign particles (e.g. asbestos). This is also the case in immunoproliferative reactions that follow the introduction into the body of an allograft and lead to its rejection.

One of the primary goals in developing effective therapies against diseases caused by unwanted or tissue damaging immunological reactions such as allograft rejection, autoimmune diseases, tissue destructive allergic reactions to infectious microorganisms or to environmental antigens, is to specifically suppress or decrease to an acceptable level the intensity of deleterious immune processes without affecting the remainder of the immune system.

The subject of immunological tolerance deals with all mechanisms that ensure an absence of destructive immune response, be it to one own's body constituents ("self antigens") or to any given foreign substance.

A long-recognized method of inducing immunological tolerance is the oral administration of antigen which was first demonstrated by Wells for hen egg proteins (Wells, H. 1911. Studies on the chemistry of anaphylaxis III. Experiments with isolated proteins, especially those of hen's egg. J. Infect. Dis. 9:147). The phenomenon, often referred to as "oral tolerance" (because initially documented by the effect of oral administration of Ag), is characterized by the fact that animals fed or having inhaled an antigen become refractory or have diminished capability to develop a systemic immune response when re-exposed to said Ag introduced by the systemic route, e.g. by injection. In broad terms, affication of an antigen onto a mucosal membrane or into a mucosal tissue, be it the intestine, the lung, the mouth, the genital tract, the nose or the eye, can induce the phenomenon of systemic immunological tolerance.

As opposed to this, introduction of an antigen into a non mucosal tissue, i.e. for example the skin or the blood, referred to as systemic immunization, often results in an immune response with the characteristics mentioned above, and is referred to as systemic immune response.

The phenomenon is highly specific of the Ag introduced by the mucosal route in the sense that hyporesponsiveness can only be documented subsequent to injection of said fed or inhaled Ag but not after injection of a structurally unrelated Ag (provided the latter had not previously been encountered at mucosal sites).

It is believed that ingested antigens are absorbed and processed by specialized cells, including epithelial enterocytes and Peyer's patch M cells, in the gut-associated lymphoid tissue (Owen, R. L., and P. Nemanic. 1978. Antigen processing structures of the mammalian intestinal tract: an SEM study of lympho-epithelial organs. Scanning Electron Microsc. 2:367–378.). It is also believed that inhaled antigens are uptaken by similar types of cells in the airway epithelium (Richardson, J., Bouchard, R. and Ferguson, C. C. 1976. Uptake and transport of exogenous proteins by respiratory epithelium. Lab. Invest. 35:307–314). Following interaction of the antigen with accessory cells and cognate helper T cells and/or B lymphocytes in the local micro-environment of the gut and of the lung mucosae, an immune response may ensue, the characteristics of which may be influenced by several factors, including the nature of the antigen, the type of accessory cells and lymphocytes involved, and the genetic background of the host. However, ingestion or inhalation of antigens may also result in the development of a state of peripheral immunological tolerance, a situation characterized by the fact that immune responses in non-mucosal tissues will not develop even if the antigen initially encountered in the digestive tract mucosa or the respiratory mucosa is reintroduced in the organism by a non-mucosal route, such as by parenteral injection. Since this phenomenon is exquisitely specific of the antigen initially ingested or inhaled, and thus does not influence the development of systemic immune responses against other antigens, its use has become an increasingly attractive strategy for preventing and possibly treating illnesses associated or resulting from the development of untoward and/or exaggerated immunological reactions against specific antigens encountered in non-mucosal tissues.

The phenomenon of mucosally induced systemic tolerance may involve all types of immune responses known to be inducible by the systemic introduction of Ag, such as the production of antibodies and the development of cell-mediated immune responses to said Ag. Mucosally induced immunological tolerance has therefore been proposed as a strategy to prevent or to reduce the intensity of allergic reactions to chemical drugs (Chase, M. W. 1946. Inhibition of experimental drug allergy by prior feeding of the sensitizing agent. Proc. Soc. Exp. Biol. 61:257–259). It has also been possible to prevent or decrease the intensity of immune reactions to systemically introduced soluble protein antigens and particulate antigens such as red cells in experimental animals and in humans by the oral administration of red cells (Thomas, H. C. and Parrot, D. M. V. 1974. The induction of tolerance to soluble protein antigens by oral administration. Immunology 27:631–639; Mattingly, J. and Waksman, B. 1978. Immunological suppression after oral administration of antigen. Specific suppressor cells found in rat Peyer's patches after oral administration of sheep erythrocytes and their systemic migration. J. Immunol. 121:1878; Bierme, S. J.; Blanc, M.; Abbal, M.; Fournie, A. 1979. Oral Rh treatment for severely immunized mothers. Lancet, 1:605–606).

The phenomenon of mucosally induced systemic tolerance can be utilized to reduce or suppress immune responses not only against foreign antigens but also against self antigens, i.e. components derived from host tissues. It has thus been possible to decrease the intensity of experimentally induced autoimmune diseases in a variety of animal systems by mucosal deposition of autoantigens onto the intestinal (by feeding) or the respiratory mucosa (by aerosolization or intranasal instillation of antigens). Thus, oral administration of collagen type II (a prominent type of collagen found in joint cartilage) has been shown to suppress or decrease the intensity of experimental autoimmune arthritis, a disease that can be induced in certain strains of rodents by injection of collagen type II together with Freund's complete adjuvant or by injection of *Mycobacterium tuberculosis* (a component of the former adjuvant) alone (Thompson, H. S. G. and Staines, N. A. 1986. Gastric administration of type II collagen delays the onset and severity of collagen-induced arthritis in rats. Clin. Exp. Immunol. 64:581; Nagler-Anderson, C., Bober, L. A., Robinson, M. E., Siskind G. W., Thorbecke, G. J. 1986. Suppression of type II collagen-induced arthritis by intragastric administration of soluble type II collagen. Proc. Natl. Acad. Sci. USA 83:7443; Zhang, J. Z., Lee, C. S. Y., Lider, O. and Weiner, H. L. 1990. Suppression of adjuvant arthritis in Lewis rats by oral administration of type II collagen. J. Immunol. 145:2489–2493). Similarly, it has been possible to suppress an experimental form of autoimmune uveoretinitis by oral administration of S-antigen, a retinal autoantigen that can induce a form of uveoretinitis when injected in animals (Nussenblatt, R. B., Caspi, R. R., Mahdi, R., Chan, C. C., Roberge, R., Lider, O., Weiner, H. L. 1990. Inhibition of S-antigen induced experimental autoimmune uveoretinitis by oral induction of tolerance with S-antigen. J. Immunol. 144:1689–1695). Experimental autoimmune encephalitis, a chronic relapsing demyelinating disorder that can be induced in certain strains of rodents by injection of purified myelin basic protein or crude spinal cord homogenate together with adjuvant, can be suppressed partially or completely if animals are given MBP or MBP fragments by the oral (feeding) or respiratory (aerosol) route (Bitar, D. M. and Whitacre, C. C. 1988. Suppression of autoimmune encephalomyelitis by the oral administration of myelin basic protein. Cell Immunol. 112:364; Higgins, P. J. and Weiner, H. L. 1988. Suppression of experimental autoimmune encephalitis by oral administration of myelin basic protein and its fragments. J. Immunol. 140:440–445; Weiner, H. L., Al-Sabbagh, A. and Sobel, R. 1990. Antigen driven peripheral immune tolerance: suppression of experimental autoimmune encephalomyelitis (EAE) by aerosol administration of myelin basic protein. FASEB J. (Abstr.) 4(7):2102). Furthermore, oral administration of insulin has been reported to suppress autoimmune diabetes in mice (Zhang, Z. J., Davidson, L., Eisenbarth, G. and Weiner, H. L. 1991. Suppression of diabetes in non obese diabetic mice by oral administration of porcine insulin. Proc. Natl. Acad. Sci. (USA) 88:10252–10256). More recently, suppression of experimental autoimmune myasthenia gravis has been achieved after oral administration of acetylcholine receptor (Wank, Z. Y., Qiao, J. and Link, H. 1993. Suppression of experimental autoimmune myasthenia gravis by oral administration of acetylcholine receptor. J. Neuroimmunol. 44:209–214).

It has also been shown that the enteric administration of schistosome eggs in mice could prevent the development or decrease the intensity of hepatic and intestinal granulomatous reactions, which are chronic T cell-mediated inflammatory immune reactions that develop around schistosome eggs during infestation by the parasite *Schistosoma* (Weinstock, J. V., Blum, A. M. and Kassab, J. T. 1985. Induction of granuloma modulation in murine schistosomiasis mansoni by enteric exposure to schistosome eggs. J. Immunol. 135:560–563).

Much in the same way, oral administration of antigens has been proposed to prevent and/or treat allergic reactions to common allergens such as house dust components or substances present in grass pollen (Rebien W., Puttonen, E., Maasch, H. J., Stix, E. and Wahn, U. 1982. Clinical and immunological response to oral and subcutaneous immunotherapy with grass pollen extracts. A prospective study. Eur. J. Pediatry 138:341–344; Wortmann F. 1977. Oral hyposensitization of children with pollinosis or house dust asthma. Allergol et Immunopathol 5:15–26).

Although the above examples indicate that mucosal administration of foreign as well as self antigens offers a convenient way for inducing specific immunologic tolerance, the applicability to large scale therapy in human and veterinary medicine remains limited by practical problems.

Indeed, to be clinically broadly applicable, mucosally-induced immunological tolerance must also be effective in patients in whom the disease process has already established itself and/or in whom potentially tissue-damaging immune cells already exist. This is especially important when considering strategies of tolerance induction in patients suffering from or prone to an autoimmune disease, an allergic condition, or a chronic inflammatory reaction to a persistent microorganism. Current protocols of mucosally induced tolerance have had limited success in suppressing the expression of an already established state of systemic immunological sensitization (Hansson, D. G., Vaz, N. M., Rawlings, L. A. and Lynch, J. M. 1979. Inhibition of specific immune responses by feeding protein antigens. II. Effects of prior passive and active immunization. J. Immunol. 122:22612266).

Most importantly, and by analogy with mucosal vaccines aimed at inducing immune responses to infectious pathogens, induction of systemic immunological tolerance by mucosal application of most antigens requires considerable amounts of tolerogen/antigen and, unless the tolerogen/antigen is administered repeatedly over long periods of time is of relatively short duration. A likely explanation is that most antigens are extensively degraded before entering a mucosal tissue and/or are absorbed in insufficient quantities. It has thus been widely assumed that only molecules with known mucosa-binding properties (examples of mucosa-binding molecules are listed in Table I below, see also reviews such as Mirelman, D. 1986. Microbial lectins and agglutinins, Properties and biological activity, pp. 84–110. Wiley, N.Y.) can induce local and systemic immune responses when administered by a mucosal route, such as the oral route, without inducing systemic immunological tolerance (de Aizpurua, H. J. and Russell-Jones, G. J. 1988. Oral vaccination. Identification of classes of proteins that provoke an immune response upon oral feeding. J. Exp. Med. 167:440–451). A notable example is cholera toxin, one of the most potent mucosal immunogens known so far (Elson, C. O. and Ealding, W. 1984. Generalized systemic and mucosal immunity in mice after mucosal stimulation with cholera toxin. J. Immunol. 132:2736) and which when administered simultaneously with an unrelated antigen by the oral route can also prevent induction of systemic immunological tolerance to said antigen (Elson, C. O. and Ealding, W. 1984. Cholera toxin did not induce oral tolerance in mice and abrogated oral tolerance to an unrelated antigen. J. Immunol. 133:2892).

Based on these observations, mucosal administration of antigens coupled to mucosa-binding molecules such as cholera toxin or its mucosa-binding fragment cholera toxin B subunit, has been proposed as a strategy to induce local and systemic immune responses rather than systemic tolerance (McKenzie, S. J. and Halsey, J. F. 1984. Cholera toxin B subunit as a carrier protein to stimulate a mucosal immune response. J. Immunol. 133:1818–1824; Nedrud, J. G., Liang, X., Hague, N. and Lamm, M. E. 1987. Combined oral/nasal immunization protects mice from Sendai virus infection. J. Immunol. 139:3484–3492; Czerkinsky, C., Russell, M. W., Lycke, N., Lindblad, M. and Holmgren, J. 1989. Oral administration of a streptococcal antigen coupled to cholera toxin B subunit evokes strong antibody responses in salivary glands and extra-mucosal tissues. Infect. Immun. 57:1072–1077; de Aizpurua, H. J. and Russell-Jones, G. J. 1988. Oral vaccination. Identification of classes of proteins that provoke an immune response upon oral feeding. J. Exp. Med. 167:440–451; Lehner, T., Bergmeyer, L. A., Panagiotidi, C., Tao, L., Brookes, R., Klavinskis, L. S., Walker, P., Walker, J., Ward, R. G. et al. 1992. Induction of mucosal and systemic immunity to a recombinant simian immunodeficiency viral protein. Science 258(5036):1365–1369).

DESCRIPTION OF THE INVENTION

As opposed to the established opinion that mucosal administration of antigens coupled to mucosa-binding molecules induce local and systemic immune responses, the present inventors have surprisingly found that antigens administered by various mucosal (oral, intranasal, vaginal, rectal) routes, when linked to a mucosa-binding molecule, enhanced induction of systemic immunological tolerance towards said antigens.

Thus the invention is directed to an immunological tolerance-inducing agent comprising a mucosa-binding molecule linked to a specific tolerogen.

The term "immunological tolerance" is here defined as a reduction in immunological reactivity of a host towards specific tolerated antigen(s). Such tolerated antigen is in the present specification and claims called a tolerogen, which is in agreement with established terminology.

In one embodiment of the invention said mucosa-binding molecule is selected from mucosa-binding molecules derived from mucosa-binding structures of bacterial toxins, bacterial fimbriae, viral attachment proteins and plant lectins. Preferably said mucosa-binding structures of bacterial toxins are selected from the group consisting of cholera toxin and heat-labile enterotoxin of *Escherichia coli*. In a preferred embodiment said mucosa-binding structure is a binding fragment of a toxin, especially the B subunit of cholera toxin or heat-labile enterotoxin of *Escherichia coli*.

Examples of classes and types of mucosa-binding molecules which may be used in the immunological tolerance-inducing agents of the invention are listed in Table I.

TABLE I

Examples of classes and types of mucosa-binding molecules

A. Bacterial toxins and their binding subunits or fragments e.g. Cholera toxin, cholera B subunit;

*Escherichia coli* heat-labile enterotoxin (LT), LT B subunit;

Bordetella pertussis toxin, subunits S2, S3, S4 and/or S5; Diphtheria toxin (DT), DT B fragment; Shiga toxin, Shiga-like toxins and B subunits B. Bacterial fimbriae e.g. *Escherichia coli*; K88, K99, 987P, F41, CFA/I, CFA/II, (CS1, CS2 and/or CS3), CFA/IV (CS4, CS5 and/or CS6), P fimbriae etc.;

*Vibrio cholerae* toxin-coregulated pilus (TCP), mannose-sensitive hemagglutinin (MSHA), fucose-sensitive hemagglutinin (FSHA) etc.;

Bordetella pertussis filamentous hemagglutinin;

C. Viral attachment proteins e.g. Influenza and Sendai virus hemagglutinins

HIV gp120;

D. Animal lectins and lectin-like molecules e.g. Immunoglobulins;

Calcium-dependant (C-type) lectins;

Soluble lactose-binding (S-type) lectins;

Selectins;

Collectins;

Helix pomatia hemagglutinin

E. Plant lectins e.g. Concanavalin A

Wheat-germ agglutinin

Phytohemagglutinin

Abrin

Ricin

In another embodiment of the invention the specific tolerogen, which is linked to a mucosa-binding molecule in an immunological tolerance-inducing agent of the invention is selected from specific antigens, including haptens, which cause an unwanted immune response in an individual. In a preferred embodiment of the invention said antigens are selected from the group consisting of proteins, peptides, carbohydrates, lipids and nucleic acids.

The unwanted immune response referred to can be associated with systemic antibody production and/or with delayed-type hypersensitivity, and is often associated with an autoimmune disorder, an allergic disorder, a tissue or cell graft rejection event and/or an acute or chronic inflammatory reaction or disorder. In the immunological tolerance-inducing agent according to the invention, the specific tolerogen and the mucosa-binding molecule are directly or indirectly linked to each other.

In an embodiment of the invention said tolerogen and said mucosa-binding molecule are indirectly linked to each other with the aid of a member of the group consisting of a spacer molecule, a protective vehicle containing said tolerogen/antigen, including hapten, or a hybrid molecule of said spacer molecule and said tolerogen/antigen, including hapten, derived from the expression of a fused gene or nucleotide sequence. In a preferred embodiment of the invention said spacer molecule is selected from molecules with binding affinity for either or both of said tolerogen or tolerogen-containing vehicle and said mucosa-binding molecule. A specific example of such a spacer molecule is an antibody. In a preferred embodiment of the invention the spacer molecule is or is derived from the choleratoxin binding structure of the GM1 ganglioside, galactosyl-N-acetyl-galactosaminyl-(sialyl)-galactosylglucosylceramide.

The way in which the specific tolerogen is linked to a mucosa-binding molecule in an immunological tolerance-inducing agent of the invention is not important as long as said tolerogen and said molecule can perform their respective function. Thus, they may be linked to each other directly by simple chemical procedures. Chemical procedures to couple proteins such as the B subunit of cholera toxin (CTB) or the thermolabile enterotoxin of *Escherichia coli* (LTB) to lipids, haptens, carbohydrates, nucleic acids as well as to other proteins including antibodies and synthetic peptides are well known in the art (e.g. see Carlsson, J. et al 1978. Biochem. J. 173:723–737; Cumber, J. A. et al. 1985. Methods in Enzymology 112:207–224; Walden, P. et al. 1986. J. Mol. Cell Immunol. 2:191–197; Gordon, R. D. et al. 1987. Proc. Natl. Acad. Sci. (USA) 84:308–312; Avrameas, S. and Ternynck, T. 1969. Immunochemistry 6:53; Joseph, K. C., Kim, S. U., Stieber, A., Gonatas, N. K. 1978. Proc. Natl. Acad. Sci. USA 75:2815–2819; Middlebrook, J. L. and Kohn, L. D. (eds): 1981. Receptor-mediated binding and internalization of toxins and hormones. Academic Press, New York, pp 311–350). The tolerogen can also be fused genetically to the CTB (or LTB) gene (Sanchez, J., Svennerholm, A-M and Holmgren, J. 1988. Genetic fusion of a non-toxic heat-stable enterotoxin-related deca-peptide antigen to cholera toxin B subunit. FEBS Letters 241:110–114) and the resulting chimeric gene then be expressed in a suitable expression system, such as a bacteria, a yeast or a virus. Alternatively, the tolerance inducing agent may comprise a fragment of a nucleic acid sequence (DNA or RNA) or a synthetic polynucleotide encoding the tolerogen which is then chemically coupled to the mucosa-binding molecule and administered by the mucosal route, advantage being then taken of the capacity of cells from host mucosal tissues to ensure transcription and/or translation of the corresponding gene into a mature protein (Rohrbaugh, M. L. and McGowan, J. J. 1993. Gene-transfer for therapy and prophylaxis of HIV-1 infection. Ann. N.Y. Acad. Sci. Vol 685, pp 697–712; Nabel, G. J. and Felgner, P. L., 1993. Direct gene-transfer for immunotherapy and immunization. Trends in Biotechnology Vol 11 No. 5, pp 211–215; Robinson, H. L., Hunt, L. A., Webster, R. G. 1993. Protection against a lethal influenza-virus challenge by immunization with a hemagglutinin-expressing plasmid DNA. Vaccine 11:957–960; Martinon, F., Krishnan, S., Lenzen, G., Magne, R., Gomard, E., Guillet, J. G., Levy, J. P. and Meulien, P. 1993. Eur. J. Immunol. 23:1719–1722). Yet other alternative presentation forms could consist in the incorporation of the tolerogen or its nucleic acid precursor into a protective vehicle such as a liposome or equivalent biodegradable vesicles onto which the mucosa-binding substance had been or shall be attached allowing efficient binding of the tolerogen-containing vehicle to a mucosal surface for improved tolerogenic efficacy. With this type of presentation form, the tolerogen may be either free or linked to another molecule.

The present invention is also directed to a method of inducing immunological tolerance in an individual against a specific antigen, including hapten, which causes an unwanted immune response in said individual comprising administration by a mucosal route of an immunologically effective amount of an immunological tolerance-inducing agent according to the invention to said individual. Examples of specific antigens which cause an unwanted immune response in an individual and which may form the specific tolerogen in the immunological tolerance-inducing agent of the invention are:

insulin or fragments thereof, including synthetic peptides or corresponding nucleic acid genetic information, and the immunological tolerance-inducing agent of the invention can be administered by the mucosal route to prevent or to suppress immune responses to insulin and thus to prevent or treat autoimmune diabetes;

myelin basic protein or fragments thereof, including synthetic peptides or corresponding nucleic acid genetic information, and the agent of the invention may be used to prevent or suppress immune responses to myelin basic protein and thus to prevent or treat multiple sclerosis;

single or double stranded DNA, and the agent of the invention may be administered to inhibit immune responses to self DNA for prevention and/or treatment of systemic lupus erythematosus, a disease whose immunological hallmark is the production of auto-antibodies to self DNA;

an antibody or fragments thereof, including synthetic peptides or corresponding nucleic acid genetic information, and the agent of the invention may be used to prevent immune responses to said antibody; the antibody may be an IgG molecule or a fragment of it and the immunological tolerance-inducing agent comprising whole IgG or fragment as tolerogen may then be administered by the mucosal route so as to prevent or reduce immune responses to IgG molecules as is the case in patients with rheumatoid arthritis and related conditions characterized by the presence of autoantibodies called rheumatoid factors which react with self IgG molecules;

gamma globulins or fragments thereof, including synthetic peptides or corresponding nucleic acid genetic information, and the agent of the invention may be administered by the mucosal route so as to prevent or reduce immune responses to said gamma globulins in situation where it would be advantageous such as before an intravenous injection of gamma globulins;

a transplantation antigen or fragments thereof, including synthetic peptides or corresponding nucleic acid genetic information, or a cell expressing said transplantation antigen, such as a red blood cell, a platelet or a lymphocyte, and the agent of the invention can be administered by the mucosal route so as to prevent or reduce immune responses to said transplantation antigen and thus to prevent rejection and/or prolong survival of an allograft;

an allergic substance such as ragweed pollen, and the agent of the invention can be administered by a mucosal route so as to prevent and/or reduce immune responses to said allergic substance and thus prevent or treat an allergy;

a bacterial toxin or fragments thereof, including synthetic peptides or corresponding nucleic acid genetic information, and the agent of invention may be administered by the mucosal route so as to prevent immune responses to said toxin encountered at systemic sites which may result in inflammation and tissue injury; an example of such situation is the septicemialike toxic shock syndrome induced by systemic administration of endotoxins (a group of lipopolysaccharides produced by gram negative bacteria) and certain exotoxins such as staphylococcal enterotoxins. In such situation, mucosal administration of said toxin or fragment therefrom linked to a mucosa-binding molecule in an agent of the present invention may be of use to avoid development of tissue damaging immune responses.

Experiments

The invention is exemplified by the use of CTB and of LTB as mucosa-binding molecules, and of sheep red blood cells (SRBC) and human gamma-globulins (HGG) as antigens/tolerogens. While the invention is in no way limited to tolerance induction against SRBC or HGG, these antigens are chosen as models of particulate and soluble antigens, respectively, since they are among the best characterized oral tolerogens with regard to both antibody formation and cell-mediated immune reactions, the latter reactions being typified by the classical delayed type hypersensitivity (DTH) reaction. These types of immune reactions have been implicated in the development of autoimmune diseases, allergic reactions, graft rejection and other inflammatory conditions. The invention is further exemplified by the use of myelin basic protein which, when coupled to CTB and given by the oral route of administration, can suppress experimental autoimmune encephalitis, and by the use of allogeneic mouse thymocytes which, when coupled to CTB and given orally, can prolong allograft survival.

The following experiments are provided for the purpose of illustrating the subject invention but in no way limit its scope.

Materials and methods

Mice: inbred Balb/c female mice were obtained from the Animal Care Facility of the Department of Medical Microbiology and Immunology, University of Göteborg, Sweden. Mice 6–8 weeks of age were used.

Purification of the mucosa-binding molecules CTB and LTB:

Recombinant cholera toxin B subunit (CTB) was produced in a mutant strain of *Vibrio cholerae* deleted of the cholera toxin genes and transfected with a plasmid encoding the CTB subunit (Sanchez, J. and Holmgren, J. 1989. Recombinant system for over-expression of cholera toxin B subunit in *Vibrio cholerae* as a basis for vaccine development. Proc. Natl. Acad. Sci. USA 86:481–485). Recombinant B subunit of *Escherichia coli* heat-labile enterotoxin (LTB) was produced similarly in a mutant strain of *Vibrio cholerae* deleted of the cholera toxin genes and transfected with a plasmid encoding E. *coli* LTB (Hirst, T. R., Sanchez, J. Kaper, J. B., Hardy, S. J. S. and Holmgren, J. 1984. Mechanism of toxin secretion by *Vibrio cholerae* investigated in strains harbouring plasmids that encode heat-labile enterotoxins of *Escherichia coli*. Proc. Natl. Acad. Sci. USA 81:7752–7756). In these expression Systems, CTB and LTB are recovered from bacterial growth media as secreted proteins. Bacterial cultures were centrifuged at 8000 rev per min for 20 min and the supernatants were collected and adjusted to pH 4.5 with dilute HCl. After precipitation with hexametaphosphate (final concentration 2.5 g/l) for 2 hours at 23° C. followed by centrifugation at 8000 rev per min, the pellets were dissolved with 0.1M sodium phosphate buffer, pH 8.0 and dialysed against 0.01M phosphate-buffered saline, pH 7.2. The dialysate was then centrifuged at 15 000 rev per min to remove residual insoluble material and the supernatant was further clarified by filtration through a 0.22 μm filter (Millipore, Bedford, Mass.). Finally, CTB and LTB were purified by standard gel filtration chromatography through columns of Sephadex G-100 (Pharmacia, Sweden).

Purification of human gamma-globulins (HGG):

HGG was purified from a pool of human sera by sequential precipitation with a solution of $(NH_4)_2SO_4$ (final concentration 40% vol:vol), followed by gel filtration chromatography on a column of Sephacryl S-300 HR (Pharmacia, Sweden) previously equilibrated with phosphate-buffered saline (0.2M sodium phosphate, NaCl 0.1M, pH 8.5). The resulting HGG preparation was diluted to 15 mg/ml.

Preparation of CTB-conjugated sheep red blood cells (SRBC-CTB):

Sheep red blood cells (SRBC) were stored at 4° C. in Alsevier's solution until use. Prior to being used, SRBC were washed 3 times with phosphate-buffered saline (PBS) (0.01M sodium phosphate, 0.15M NaCl, pH 7.4) by centrifugation at 3000 rev. per min. for 10 min and then resuspended at a cell density of $5 \times 10^9$ SRBC/ml in PBS. To facilitate coupling of CTB to SRBC, SRBC were first coupled to GM1 ganglioside. A solution of PBS containing 300 nmol/ml GM1 ganglioside (Sigma Chemical Co., St. Louis, Mo.) was added to packed SRBC at a ratio of 1:2 (vol/vol) and incubation was carried out at 37° C. for 2 hours in a shaking water bath. After 3 washes with PBS to remove excess GM1, GM1-coated red cells were resuspended to a density of $5 \times 10^9$ SRBC/ml in PBS and mixed with recombinant CTB (Sanchez, J. and Holmgren, J. 1989 Recombinant system for overexpression of cholera toxin B subunit in *Vibrio cholerae* as a basis for vaccine development. Proc. Natl. Acad. Sci. USA 86:481–485) (final concentration 50 μg/ml). After incubation for 2 hours at 37° C. in a shaking water bath to allow binding of CTB to GM1-coated SRBC, the red cell suspension was washed twice with PBS to remove non cell bound CTB and resuspended at a cell density of $1 \times 10^{10}$ /ml of PBS. To ascertain that the CTB molecules had bound to GM1-coupled SRBC and were still able to bind additional GM1molecules, a solid phase hemadsorption assay using GM1 immobilized on plastic wells was employed. An aliquot of red cell suspension was diluted to a final concentration of 1% (packed vol/vol) in PBS supplemented with 0.1% (weight/vol) of bovine serum albumin (BSA) (Sigma) and added to GM1-coated U-shaped wells of plastic microtiter plates (Costar). After incubation at ambient (22° C.) temperature, wells were examined for appearance of hemadsorption. The specificity of the assay was established by the absence of hemadsorption in control wells that had not been coated with GM1 and by addition of cell-free CTB to GM1-coated wells during incubation with red blood cells which prevented in a dose dependent manner hemadsorption.

Preparation of LTB-conjugated sheep red blood cells (SRBC-LTB):

GM1-coated SRBC ($5 \times 10^9$ GM1-SRBC/ml) were conjugated to recombinant LTB (50 μg/ml) exactly as described above for coupling of SRBC to CTB.

Preparation of CTB-conjugated human gamma-globulins (HGG-CTB):

CTB and HGG were each coupled to N-succinimidyl (3-(2-pyridyldithio) propionate (SPDP) (Pharmacia, Uppsala, Sweden) (Carlsson, J., H. Drewin, and R. Axen. 1978. Protein thiolation and reversible protein-protein conjugation. N-succinimidyl 3-(2-pyridyl-dithio) propionate: a new heterobifunctional reagent. Biochem. J. 173:723–737.1) at molar ratios of 1:5 and 1:10 respectively. SPDP was added to HGG and the mixture was allowed to incubate for 30 min at 23° C. with stirring. Excess SPDP was removed by gel filtration on a column of Sephadex G-25 (Pharmacia, Sweden) equilibrated with acetate buffer (0.1M sodium acetate, 0.1M NaCl, pH 4.5). The SPDP-derivatized HGG was reduced with dithiothreitol (DTT) (final concentration 50 mM) for 20 min at 23° C. and the resulting preparation was passed through a column of Sephadex G-25 equilibrated with phosphate-buffered saline (0.2M sodiumphosphate, NaCl 0.1M, pH 8.5) to remove excess DTT and pyridine-2-thione released during reduction of SPDP-derivatized HGG.

CTB was diluted to 2 mg/ml in phosphate-buffered saline (0.2M sodium phosphate, NaCl 0.1M, pH 8.5) and derivatized with SPDP as described above for HGG but at a molar ratio of 5:1 (SPDP:CTB). The resulting SPDP-derivatized CTB was passed through a column of Sephadex G-25 equilibrated in the same buffer, to remove excess unreacted SPDP.

SPDP-derivatized HGG and CTB were mixed at an equimolar ratio and incubated for 16 h at 23° C. The resulting CTB-HGG conjugate was purified by gel filtration through a column of Sephacryl S-300 to remove free CTB and/or HGG. The resulting conjugate was shown to contain $G_{M1}$ ganglioside binding capacity and to retain both CTB and HGG serological reactivities by means of an ELISA using $G_{M1}$ (Sigma, St. Louis, Mo.) as solid phase capture system (Svennerholm, A.-M., and J. Holmgren. 1978. Identification of *Escherichia coli* heat-labile enterotoxin by means of a ganglioside immunosorbent assay ($GM_1$-ELISA) procedure. Curr. Microbiol. (1:19–23), and monoclonal and polyclonal antibodies to CTB and HGG as detection reagents (see below). Serial two-fold dilutions of the conjugate and of purified CTB- and HGG-SPDP derivatives were incubated in polystyrene wells that had previously been coated with GM1 ganglioside, and in wells coated with rabbit polyclonal IgG antibodies to HGG; next, horseradish peroxidase (HRP) conjugated rabbit ant-HGG or mouse monoclonal anti-CTB antibodies, appropriately diluted in PBS containing 0.05% Tween 20, and enzyme substrate were applied sequentially to detect solid phase bound HGG and CTB. The amount of free and bound HGG and CTB was determined by reference to standard curves calibrated with known amounts of SPDP derivatized antigens. On average, the SPDP conjugation procedure and purification protocol described above yielded preparations containing negligible amounts of free HGG and less than 10% free CTB.

Immunization protocols:
Immunization with SRBC:

Primary systemic immunization: Mice were injected in the rear left footpad with 40 µl of pyrogen-free saline containing $10^7$ SRBC.

Secondary systemic immunization: Five days after the primary immunization, mice were challenged by injecting the right rear footpad with 40 µl of pyrogen-free saline containing $10^8$ SRBC.

Immunization with HGG:

Prior to immunization, HGG was aggregated by heating at 63° C. for 30 min. Primary systemic immunization: Mice received 0.2 ml of aggregated HGG (500 µg) emulsified in Freund's complete adjuvant (Difco, St. Louis, Mo.) and administered by subcutaneous injections into the flanks.

Secondary systemic immunization: Five days after the primary immunization, mice were challenged by injecting the right rear footpad with 40 µl of pyrogenfree saline containing 1 mg of HGG.

Oral tolerance induction protocols:

At various times before or after the primary systemic immunization with SRBC, mice were administered a single dose or daily consecutive doses of SRBC or SRBC-CTB. Each dose consisted of $2.5 \times 10^9$ SRBC or SRBC-CTB in 0.5 ml of PBS given by the intragastric route using a baby catheter feeding tube. Control animals were given 0.5 ml of PBS alone.

For induction of tolerance to HGG, mice were given a single oral dose of unconjugated HGG or CTB-conjugated HGG administered by intragastric tubing, 1 week before primary systemic immunization with HGG. Doses of 1 mg and 5 mg of unconjugated HGG and of 60 µg of CTB-conjugated HGG were tested.

Evaluation of delayed-type hypersensitivity (DTH) reactions:
DTH to SRBC:

Thickness of the right footpad was measured immediately before and 2, 4, 24 and 48 h after the secondary systemic immunization with SRBC, using a dial gauge caliper (Oditest, H. C. Köplin, Schluchtern, Essen, Germany). The intensity of DTH reactions was determined for each individual animal by substracting the value obtained before challenge from those obtained at various times after challenge.

DTH to HGG:

The intensity of DTH reactions to HGG injected in the right footpad was evaluated as above for SRBC.

Evaluation of serum antibody responses:
Serum anti-SRBC antibody responses:

Immediately before the primary systemic immunization with SRBC administered in the left footpad and 1–2 weeks after the secondary systemic immunization, a sample of blood was collected from the tail vein of individual mice and allowed to clot at room temperature for 60 min. Sera were heated at 56° C. for 45 min to inactivate complement and then assayed for antibody levels to SRBC by direct and indirect hemagglutination assays. For direct hemagglutination, serial 2-fold dilutions of serum samples in PBS supplemented with 0.1% (weight/vol) of bovine serum albumin (PBS-BSA) were prepared in U-bottom wells of microtiterplates. Fifty microliters of a suspension of 0.5% (packed vol/vol) SRBC in PBS-BSA was added to all wells and the plates were incubated for 1 hour at ambient temperature followed by an overnight incubation at 4° C. Wells were then examined for hemagglutination.

To detect non-hemagglutinating antibodies that had bound to SRBC, 25 µl of PBS containing a mixture of heat-inactivated (56° C. for 45 min) rabbit antisera to mouse IgG and mouse IgA (final dilution 1:50) was added to wells corresponding to serum dilutions negative in the direct hemagglutination assay. The plates were then shaken to allow resuspension of SRBC and incubated undisturbed at 4° C. for 2 hours. Thereafter the wells were examined for hemagglutination. The reciprocal of the highest dilution of any given mouse serum causing hemagglutination of SRBC either directly or after addition of anti-mouse antisera (in the indirect hemagglutination assay) was determined and defined as the anti-SRBC antibody titer of said mouse serum.

Serum anti-HGG antibody responses:

Serum IgM and IgG antibody levels to HGG were determined by standard solid phase ELISA using polystyrene microwells coated with HGG as solid phase capture system and HRP-conjugated affinity purified goat antibodies to mouse IgG and to mouse IgM (Southern Biotechnology Associates, Birmingham, Ala.) as detection reagents. Serial 5-fold dilutions of mouse sera were prepared in PBS containing 0.05% Tween 20 and incubated for 2 hrs at 23° C. in HGG-coated wells. After 5 washings with PBS containing 0.05% Tween 20, appropriately diluted HRP-antibodies to mouse IgM or IgG were added. Two hours later, plates were rinsed with PBS and solid phase bound enzyme activity was revealed by addition of chromogen substrate, consisting of ABTS tablets (Southern Biotechnology Associates) dissolved in citrate-phosphate buffer, pH 5.0 and containing $H_2O_2$. Absorbance values were monitored 30 min later with an automated spectrophotometer (Titerscan, Flow Laboratories). The anti-HGG antibody titer of a mouse serum was defined as the reciprocal of the highest dilution given an absorbance value of at least twice that of control wells exposed to buffer alone instead of serum.

In vitro lymphocyte proliferation assay:

Lymph nodes obtained 1–2 weeks after the secondary systemic immunization were minced in Iscove's medium (Gibco Europe, U. K.) and pressed through sterile nylon-mesh screens to yield single cell suspensions. The cells were washed twice and resuspended at $2 \times 10^6$ cells/ml in Iscove's medium supplemented with 5% heat-inactivated fetal bovine serum (FBS), L-glutamine (1%), sodium pyruvate (1%), non-essential aminoacids (1%), 2-mercaptoethanol ($5\times10^{-5}$M) and gentamycin (20 µg/ml). Lymph node cells were added to flat-bottom microtiter (Nunc, Denmark) wells containing a previously titrated amount of SRBC in a total volume of 200 ml. The plates were then incubated at 37° C. in 5% $CO_2$ in air for 3 days. The cultures were pulsed during the last 16 hrs with $^3$H-thymidine (2.0 mCi/mM, Amersham, Stockholm), individual wells were harvested using a 96-well automated cell-harvester (Inotech, Basel, Switzerland) and the radio-nucleotide incorporation was measured with an argon-activated scintillation counter (Inotech).

The level of $^3$H-thymidine incorporation was calculated as the stimulation index (S.I.)=CPM of lymph node cells+ SRBC/CPM of lymph node cells alone.

EXAMPLE 1

Prevention of early and late delayed-type hypersensitivity (DTH) reactions by oral administration of sheep red blood cells (SRBC) linked to the B subunit of cholera toxin (CTB):

Mice were fed a single dose of SRBC-CTB, SRBC alone, or saline which was given 1 to 8 weeks before a primary systemic immunization with SRBC injected in the left rear footpad. Five days after this injection, the right rear footpad was challenged so as to elicit a DTH reaction. The intensity of DTH reactions elicited in mice fed SRBC alone was comparable to that recorded in control mice fed saline only (Table 2). In contrast, DTH reactions recorded in mice fed SRBC conjugated to the mucosa-binding molecule CTB were considerably decreased, at all times recorded. Thus, 2 hours after challenge with SRBC, that is at a time corresponding to the early peak of DTH responses seen in control (saline fed only) animals, footpad swelling was absent in mice previously fed a single dose of SRBC-CTB. Furthermore, the late DTH response which in mice peaks at 24 hours post-challenge was significantly decreased as compared to saline fed control animals as well as to animals fed SRBC alone.

In a second set of experiments, mice were fed single or daily consecutive doses of SRBC-CTB or SRBC. One week after the last oral administration, animals were primed and challenged as above by systemic injections of SRBC in the left footpad followed 5 days later by the right footpad. It was found that the daily oral administration of SRBC for 3-4 weeks was required to suppress the 24 hr DTH reactions to a level comparable to that achieved by a single administration of SRBC conjugated to CTB (Table 3). It should however be pointed out that as many as 20 consecutive feedings with SRBC over a 4 week period had no effect on the development of the early phase (2-4 hours) of the DTH response, in contrast to the situation seen with animals fed a single dose of SRBC conjugated to CTB who failed to develop an early DTH response.

EXAMPLE 2

Inhibition of early and late DTH reactions by oral administration of sheep red blood cells (SRBC) linked to the B subunit of cholera toxin (CTB) in immune mice:

To determine whether mucosal administration of CTB-conjugated antigens would suppress DTH reactions in animals previously systemically sensitized to said antigen, SRBC were first injected in the left rear footpad of mice to induce a state of primary systemic immunity. Four days later, animals were fed a single oral dose of SRBC conjugated to CTB, SRBC alone, or saline. Two days after the latter feeding, animals were given a second injection of SRBC in the right footpad to elicit DTH reactions. The latter DTH responses were monitored at various times after this secondary systemic immunization. Whereas mice fed SRBC alone developed DTH responses undistinguishable from those seen in control animals fed only saline, mice fed SRBC conjugated to CTB had considerably reduced early and late DTH responses to SRBC. Therefore, it appears that oral administration of SRBC conjugated to CTB can induce suppression of both early and late DTH responses to systemically injected SRBC even in animals previously sensitized (primed) systemically to SRBC.

EXAMPLE 3

Inhibition of lymphocyte proliferation by oral administration of sheep red blood cells (SRBC) linked to the B subunit of cholera toxin (CTB)

To determine whether oral administration of CTB-conjugated antigens would result in decreased proliferative responses of lymph node cells to said antigens, mice were fed a single dose of CTB-conjugated SRBC and were then injected in the left footpad with SRBC (primary systemic in vivo immunization). One week later, the ability of lymph node cells to proliferate after in vitro exposure to the homologous antigen (SRBC) was examined. Compared to control animals fed saline only and to animals fed a single dose of SRBC alone, lymph node cells from animals fed SRBC conjugated to CTB had decreased proliferative responses when cultured with SRBC (Table 4). This decrease was specific of the antigen administered in as much as the proliferative responses of lymph node cells to the mitogen concanavalin A were comparable in animals fed SRBC-CTB, SRBC or saline only (Table 4).

EXAMPLE 4

Inhibition of serum antibody responses by oral administration of sheep red blood cells (SRBC) linked to the B subunit of cholera toxin (CTB)

To determine whether oral administration of an antigen coupled to CTB would result in decreased antibody responses to systemically administered antigen, mice were fed a single dose of SRBC-CTB, SRBC alone, or saline which was given 1 to 8 weeks before a primary systemic immunization with SRBC injected in the left rear footpad. Five days after this injection, the right rear footpad was challenged and blood was collected from the tail vein 1 week later. Serum antibody levels to SRBC were determined by direct and indirect hemagglutination assays. As seen in Table 5, serum antibody responses to SRBC were decreased in animals fed a single dose of SRBC-CTB as compared to animals fed saline only or a single dose of SRBC alone. Daily oral administrations of SRBC for 3 weeks were required to suppress serum antibody responses to systemically administered SRBC to a level comparable to that achieved by a single administration of SRBC conjugated to CTB (Table 5).

EXAMPLE 5

Inhibition of early and late DTH reactions by oral administration of sheep red blood cells (SRBC) linked to the B subunit of *Escherichia coli* heat-labile enterotoxin B subunit (LTB):

To determine whether mucosal administration of SRBC conjugated to another mucosa-binding molecule, the B subunit of *Escherichia coli* heat-labile enterotoxin B subunit (LTB), would also suppress DTH reactions to systemically administered SRBC, mice were fed a single dose of SRBC- LTB or saline, which was given 1 week before a primary footpad injection with SRBC. For comparative purposes, an additional group of mice was fed with SRBC-CTB. Five days after the primary injection, all mice were challenged with SRBC in the contralateral footpad so as to elicit a DTH reaction. At 24 hr post-challenge, DTH reactions recorded in mice fed SRBC-LTB were significantly reduced as compared to saline fed control mice (Table 6). However, the early (2–4 hrs) DTH reactions were not reduced in mice fed SRBC-LTB. This contrasted with DTH reactions recorded in mice fed SRBC-CTB which were absent at 2–4 hrs post-challenge and were significantly reduced at 24–48 hrs (Table 6). These observations indicate that oral administration of SRBC conjugated to LTB can induce suppression of the late DTH response to systemically injected SRBC but does not affect the early component of such responses.

EXAMPLE 6

Inhibition of early and late delayed-type hypersensitivity (DTH) reactions to human gamma globulins (HGG) by oral administration of HGG conjugated to the B subunit of cholera toxin (CTB):

To determine whether mucosal administration of CTB-conjugated antigens would suppress DTH reactions to a soluble protein antigen, mice were fed a single dose of HGG conjugated to CTB, HGG alone, or saline. These were given to separate groups of mice 1 week before a primary systemic immunization with HGG in Freund's complete adjuvant injected subcutaneously. Five days after this injection, the right rear footpad was challenged with HGG so as to elicit a DTH reaction. The intensity of DTH reactions elicited in mice fed 1 mg of HGG alone was comparable to that in control mice fed saline only, at all times examined after challenge (Table 7). Feeding mice 5 mg of HGG resulted in decreased DTH reactions at 24–48 hrs but did not influence the intensity of the early (2–4 hrs) phase of these reactions. In contrast, DTH reactions monitored in mice fed as little as 15 μg of HGG conjugated to CTB, that is a more than 300-fold lower amount of HGG, had similar effects, being significantly lower than corresponding reactions in control (saline fed) animals at 24 hrs, but not at earlier times (2 and 4 hrs). However, feeding mice with 66 μg of HGG conjugated to CTB resulted in considerably decreased DTH reactions at all times recorded. Thus, the early (2–4 hr) and late (24–48 hr) DTH reactions were virtually abrogated in mice fed 66 μg of HGG conjugated to CTB. These observations demonstrate that oral administration of small amounts of a soluble protein antigen conjugated to the mucosa-binding molecule CTB can induce suppression of both early and late DTH reactions to subsequent systemic injection with said protein antigen.

EXAMPLE 7

Suppression of experimental autoimmune encephalitis (EAE) by oral administration of myelin basic protein conjugated to CTB.

Purification of myelin basic protein (MBP):

MBP was obtained from guinea pig spinal cord and brain as described by Deibler et al (Deibler, G. E., Martenson, R. E., Kies, M. W. 1972. Large scale preparation of myelin basic protein from central nervous tissue of several mammalian species. Prep. Biochem. 2:139–165). Purity of MBP was determined by standard sodium dodecyl sulphate polyacrylamide which showed a single band at approximately 20 kD. MBP was coupled to CTB by the SPDP procedure under conditions similar to those described for conjugating HGG to CTB. The presence of MBP in the conjugated material was ascertained by GM1-ELISA using serum from a rat immunized with MBP in FCA. The relative proportions of MBP and CTB in the conjugates were determined by comparisons with purified preparations of CTB and MBP assayed in parallel by standard solid phase sandwich ELISA (for MBP) and GM1-ELISA (for CTB) using anti-MBP and GM1 as solid phase capture reagents, and HRP-conjugated rat anti-MBP antiserum and mouse anti-CTB monoclonal antibodies to detect captured MBP and CTB, respectively.

Induction of experimental autoimmune encephalitis (EAE): To induce EAE (Kies, M. W., Murphy, J. B., Alvord, E. C. 1960. Fractionation of guinea pig proteins with encephalitogenic activity. Fed. Proc. 19:207), female Lewis rats (ZentralInstitut für Versuchstierzucht, Hannover, Germany), 8–10 weeks old (weight 170–240 g), were injected under ether anaesthesia in both rear hind footpads with a total of 100 microgram (that is approximately 50 micrograms by footpad) of guinea pig MBP emulsified in Freund's complete adjuvant (FCA) (Difco, Detroit, Mich., USA) (1:1, vol:vol). After this injection, animals were followed daily for 30 days. Every second day, animals were examined for appearance of clinical symptoms and their body weight determined. Disease intensity was determined using a standard clinical grading system (Miller, A., Lider, O., AlSabbagh, A., Weiner, H. L. 1992. Suppression of experimental autoimmune encephalomyelitis by oral administration of myelin basic protein. V. Hierarchy of suppression by myelin basic protein from different species. J. Neuroimmunol. 39:243–250):

grade 0: no disease grade 1: limp tail grade 2: mild hind limb paralysis grade 3: severe hind limb paralysis with limbs splayed apart grade 4: complete hind limb paralysis affecting all four footpads grade 5: death Oral tolerance protocols:

Before induction of EAE by footpad injection of MBP, separate groups of animals were given the following regimens:
    group 1:0.5 ml of MBP-CTB conjugate corresponding to 20 micrograms of MBP and 100 micrograms of CTB in 0.6M bicarbonate buffer given on day −7 before footpad injection of MBP (referred to as day 0 thereafter);

group 2:0.5 ml of 0.6M bicarbonate buffer containing 5 mg MBP and 10 mg of soybean trypsin inhibitor (STI) to minimize proteolytic degradation of MBP (Whitacre, C. C., Gienap, I. E., Orosz, C. G., Bitar, D. 1991. Oral tolerance in experimental autoimmune encephalitis. III. Evidence for clonal anergy. J. Immunol. 147:2155–63), 5 consecutive times on day −11, −9, −7, −5, and −3 before footpad injection with MBP;

group 3:0.5 ml of saline (control) on 5 consecutive occasions according to the time-table defined for group 2;

group 4:0.5 ml of 0.6M bicarbonate containing 10 mg soybean trypsin inhibitor (STI) alone (control) on 5 consecutive occasions according to the time-table described for group 2.

Suppression of EAE by oral administration of MBP conjugated to CTB:

Groups consisting of 5 adult female Lewis rats were injected in the rear footpads with MBP emulsified in FCA or with FCA alone. In control animals previously fed with soybean trypsin inhibitor (STI) (group 4), given 11, 9, 7, 5 and 3 days before footpad injection with MBP+FCA, neurological symptoms developed being maximal 12 to 14 days after the injection and all animals developed severe paralysis (Table 8). Animals fed as little as 20 micrograms of MBP conjugated to CTB administered in a single dose (group 1), developed either no (4 out of 5 rats) or mild symptoms (transient tail paresis associated with right hind footpad paresis in another rat) (Table 8). Animals fed 5 milligram of MBP together with STI on 5 consecutive occasions, that is a total of 25 mg MBP or 1250 times higher doses of MBP than group 1 animals, were also protected from developing severe EAE disease (group 2) (Table 8). Thus, oral administration of small amounts of MBP conjugated to CTB can suppress EAE.

EXAMPLE 8

Prolongation of mouse allograft survival by oral administration of allogeneic thymocytes conjugated to cholera toxin B subunit (CTB).

Conjugation of mouse thymocytes with CTB:

To enhance binding of CTB to mouse lymphocytes, thymocytes from C57BL/6 mice (major histocompatibility complex (MHC) haplotype H-$2^b$) were first derivatized with GM1 ganglioside by mixing 5×$10^7$ thymocytes with 10 nanomoles of GM1 ganglioside in a total volume of 0.5 ml of Iscove's minimal essential medium (IMEM) for 2 hrs at 37° C. Cells were then washed 3 times with pyrogen-free sterile saline to remove unbound GM1 and incubated for a further 2 hours at 37° C. with 25 micrograms of CTB in a final volume of 0.5 ml. Finally, cells were washed with saline to remove unbound excess CTB and kept on ice until use. These concentrations of GM1 and CTB were required to achieve maximal saturation of thymocytes as determined by flow cytometric analysis of mouse thymocytes derivatized with various amounts of GM1 and exposed to various concentrations of tetramethyl rhodamine-labelled CTB (List Biological Laboratories Inc., Campbell, Calif., USA).

Heterotopic mouse cardiac grafts:

Donor hearts were collected from newborn (less than 36 hours after birth) C57BL/6 mice and sectioned along the ventricular septum. Each half of the heart was inserted into a subcutaneous pouch on the dorsal part of one ear or both ears of 6- to 8-week old Balb/c mice (MHC haplotype H-$2^d$). For comparative purposes, a separate group of Balb/c recipient mice received hearts from syngeneic Balb/c newborn mice. Graft function was assessed daily by measuring the electric activity of the transplants with a Tektronix cardioscope. Rejection time was defined as the day when complete cessation of myocardial contraction had occurred.

Oral tolerance protocols:

Before and/or at various times after allograft implantation, adult Balb/c mouse recipients were fed with a baby catheter feeding tube a volume of 0.5 ml of pyrogen-free saline containing either:

unconjugated thymocytes from newborn C57BL/6 mice given 3 days before and 1 and 4 days after transplantation;

unconjugated thymocytes from newborn C57BL/6 mice given 7, 4 and 1 day before transplantation;

CTB-conjugated thymocytes from newborn C57BL/6 mice given 7, 4 and 1 day before transplantation;

CTB-conjugated thymocytes from newborn C57BL/6 mice given immediately before (30–60 minutes) transplantation;

or saline only.

Prolongation of survival of mouse heterotopic cardiac allografts by oral administration of allogeneic thymocytes conjugated to cholera toxin B subunit (CTB):

Balb/c mice receiving heterotopic cardiac grafts from newborn C57BL/6 donor mice histoincompatible at the H-2 locus rejected their grafts on average within 8 days (Table 9). In contrast, mice receiving H-2 histocompatible cardiac grafts maintained functional transplants for more than 2 months. Oral administration of thymocytes from newborn H-2 histoincompatible mice of the same species as donor mice either before (day −7, −4 and −1) and/or after (−3, +1 and +4) implantation of heart allografts did not prolong and in some instances did even reduce graft survival in Balb/c mouse recipients (Table 9). In contrast, oral administration of 3 doses of thymocytes conjugated to CTB before (day −7, −4 and −1) allograft implantation, substantially increased (mean 56%) survival of cardiac grafts (Table 9). Furthermore, a single oral dose of CTB-conjugated C57BL/6 thymocytes given shortly before transplantation prolonged (mean 39%) graft survival in mouse recipient of allogeneic heart transplants (Table 9). Taken together, the results of these experiments demonstrate that oral administration of histoincompatible lymphocytes conjugated with CTB can prolong allograft survival.

TABLE 2

Prevention of early and late delayed-type hypersensitivity reactions by oral administration of sheep red blood cells (SRBC) linked to the B subunit of cholera toxin (CTB)

| feeding | number of feedings | mean footpad thickness increment × $10^{-3}$ cm (± 1 standard deviation) | | |
|---|---|---|---|---|
| | | 4 hrs | 24 hrs | 48 hrs |
| SRBC-CTB | 1 | 11 ± 2.0* | 23 ± 12.1** | 16 ± 4.6* |
| SRBC | 1 | 45 ± 4.2 | 50 ± 10.6 | 30 ± 4.6 |
| SRBC | 5 | 34 ± 9.1 | 59 ± 6.0 | 34 ± 6.1 |
| SRBC | 10 | 34 ± 7.6 | 41 ± 3.8 | 29 ± 8.6 |
| SRBC | 15 | 32 ± 7.4 | 33 ± 8.1* | 24 ± 6.3 |
| SRBC | 20 | 31 ± 13.0 | 25 ± 5.5** | 16 ± 4.4* |
| saline | | 35 ± 10.8 | 50 ± 12.7 | 32 ± 8.3 |

Asterisks denote significant differences between values determined on test groups (6 animals per group) and on control group consisting of animals (7 mice) fed saline only: *, p < 0.05 and ** p < 0.01 (Student't test).

TABLE 3

Inhibition of early and late DTH reactions by oral administration of sheep red blood cells (SRBC) linked to the B subunit of cholera toxin (CTB) in immune mice

| systemic sensitization with SRBC (day 0) | feeding (day 4) 1 dose of: | mean footpad thickness increment × $10^{-3}$ cm (± 1 standard deviation) after systemic challenge with SRBC (day 7) | | |
|---|---|---|---|---|
| | | 4 hrs | 24 hrs | 48 hrs |
| + | SRBC-CTB | 23 ± 3.3** | 20 ± 7.1** | 12 ± 3.8* |
| + | SRBC | 50 ± 8.2 | 44 ± 7.4 | 28 ± 5.4 |
| + | saline | 61 ± 7.4 | 53 ± 4.7 | 25 ± 6.2 |
| − | saline | 28 ± 1.0 | 29 ± 0.5 | 12 ± 3.5 |

Asterisks denote significant differences between values determined on test groups (6 animals per group) and on control group (6 mice) consisting of animals sensitized with SRBC but fed saline only before challenge:
*p < 0.05 and **p < 0.01 (Student't test).

TABLE 4

Inhibition of antigen specific lymphocyte proliferation by oral administration of sheep red blood cells (SRBC) linked to the B subunit of cholera toxin (CTB)

| feeding one dose of: | mean S. I. values ± 1 standard deviation in cultures exposed to | |
|---|---|---|
| | SRBC | concanavalin A |
| SRBC-CTB (n = 6 mice) | 1.06 ± 0.29* | 119 ± 32 |
| SRBC (n = 6 mice) | 7.88 ± 4.52 | 108 + 56 |
| saline (n = 6 mice) | 8.94 ± 3.89 | 76 ± 35 |

*denotes significant difference (P < 0.01; Student't test) between test SRBC-CTB fed animals and animals fed SRBC alone or fed saline only.

TABLE 5

Inhibition of serum antibody responses to SRBC after oral administration of SRBC linked to the B subunit of cholera toxin (CTB)

| feeding 1 dose of: | mean serum anti-SRBC titers ± 1 standard deviation |
|---|---|
| SRBC-CTB | 40 ± 20* |
| SRBC | 1000 ± 250 |
| nil | 1000 ± 200 |

*denotes significant difference (P < 0.001; Student't test) between

TABLE 6

Prevention of late delayed-type hypersensitivity reactions by oral administration of sheep red blood cells (SRBC) linked to the B subunit of Escherichia coli heat-labile entero-toxin B subunit (LTB)

| | mean footpad thickness increment × $10^{-3}$ cm (± 1 standard deviation) | | | |
|---|---|---|---|---|
| feeding | 2 hrs | 4 hrs | 24 hrs | 48 hrs |
| SRBC-LTB | 4 ± 10 | 16 ± 8.2 | 38 ± 12* | 13 ± 2.2* |
| SRBC-CTB | 0 ± 0* | 6 ± 5.4* | 22 ± 6.7* | 7.1 ± 3** |
| saline | 7 ± 5.5 | 14 ± 2.3 | 50 ± 4.3 | 24 ± 3.5 |

Asterisks denote significant differences between test groups (7 mice per group) and control animals (n = 6 mice) fed saline only: *p < 0.05 and **p < 0.01 (Student't test).

TABLE 7

Prevention of early and late delayed-type hypersensitivity reactions by oral administration of human gamma-globulins (HGG) linked to the B subunit of cholera toxin (CTB)

| Group | feeding | §sensi-tization | mean footpad thickness increment × $10^{-3}$ cm (±1 standard deviation) after systemic challenge with HGG ¶ | | | |
|---|---|---|---|---|---|---|
| | | | 2hrs | 4hrs | 24hrs | 48hrs |
| I | HGG (66 µg)-CTB | + | 18 ± 5.1* | 45 ± 7* | 30 ± 6.2** | 26 ± 4.5* |
| II | HGG (15 µg)-CTB | + | 38 ± 8.4 | 68 ± 7.1 | 34 ± 3.2** | 27 ± 4.4* |
| III | HGG 5 mg | + | 40 ± 7.6 | 51 ± 13 | 37 ± 5** | 28 ± 1.9* |
| IV | HGG 11 mg | + | 38 ± 5.5 | 57 ± 17 | 45 ± 7.4 | 36 ± 6.8 |
| V | saline | + | 39 ± 8.7 | 59 ± 5.8 | 51 ± 2.9 | 39 ± 12 |
| VI | saline | − | 23 ± 5.7 | 43 ± 18 | 22 ± 8 | 17 ± 2.5 |

§Animals were sensitized by subcutaneous injection of 0.5 mg heat-aggregated HGG in Freund's complete adjuvant.
¶Animals were challenged by injecting the right footpad with 1 mg HGG in saline.
Asterisks denote significant differences beween test groups (group I–IV, n = 6 mice per group) and control animals fed saline only (group V, n = 6 mice): *p < 0.05 and **p < 0.01 (Student't test).

TABLE 8

Suppression of experimental autoimmune encephalitis (EAE) in Lewis rats by oral administration of myelin basic protein conjugated to CTB

| animal group | feeding | number of doses | footpad injection | clinical score of EAE | incidence of paralysis[a] |
|---|---|---|---|---|---|
| 1 | MBP (20 µg)-CTB | 1 | MBP + FCA | 1.1 ± 0.4 | 0/5 |
| 2 | MBP 5 mg (+STI) | 5 | MBP + FCA | 0.6 ± 0.5 | 0/5 |
| 3 | saline | 5 | FCA | 0 | 0/5 |
| 4 | STI | 5 | MBP + FCA | 3.9 ± 0.5 | 5/5 |

[a]Clinical grade ≧ 2

TABLE 9

Prolongation of survival of mouse heterotopic cardiac allografts by oral administration of allogeneic thymocytes conjugated to cholera toxin B subunit (CTB)

| donor of heart transplant (MMC class II haplotype) | feeding[a] | feeding day | mean rejection time ± standard deviation (days) | number of heart transplants | % increased graft survival time[b] |
|---|---|---|---|---|---|
| C57BL/6 (H-$2^b$) | thymocytes | −3, +1, +4 | 7.9 ± 1.0 | 8 | −4,8% |
| C57BL/6 (H-$2^b$) | thymocytes | −7, −4, −1 | 6.5 ± 0.5 | 10 | −21% |
| C57BL/6 (H-$2^b$) | CTB (25 microgram)-conjugated thymocytes | −7, −4, −1 | 13 ± 0 | 16 | 56% |
| C57BL/6 (H-$2^b$) | CTB (25 microgram)-conjugated thymocytes | 0 | 11.6 ± 1.3 | 14 | 39% |
| C57HL/6 (H-$2^b$) | saline | 0 | 8.3 ± 1.3 | 19 | 0% |

TABLE 9-continued

Prolongation of survival of mouse heterotopic cardiac allografts by oral administration of allogeneic thymocytes conjugated to cholera toxin B subunit (CTB)

| donor of heart transplant (MMC class II haplotype) | feeding[a] | feeding day | mean rejection time ± standard deviation (days) | number of heart transplants | % increased graft survival time[b] |
|---|---|---|---|---|---|
| Balb/c (H-2$^d$) syngeneic control | saline | 0 | >64 | 26 | |

[a]Adult Balb/c mouse recipients were fed 5 × 10$^7$ newborn thymocytes alone or conjugated to CTB (25 micrograms per mouse) on the indicated days and received heart transplants on day 0.
[b]Relative increase in graft survival was calculated as follows: (mean rejection time of mice fed thymocytes minus mean rejection time of saline fed control mice divided by mean rejection time of saline fed control mice) × 100.

As is evident from the above examples, the immunological tolerance-inducing agent of the invention is efficient at suppressing induction and preventing expression of systemic immune responses. Further, it minimizes the absolute amount of antigen/tolerogen and/or numbers of doses that would be required by reported protocols of orally-induced tolerization. As inferred from the above examples, the immunological tolerance-inducing agent of the invention can be used to prevent or delay the development of inflammatory immune responses associated with the early and late phases of delayed type hypersensitivity reactions, en auto immune disease (example 8) and the rejection or an allograft (example 9).

We claim:

1. A method of inducing immunological tolerance in a mammal to a T-cell-associated immunological response, which comprises administering by a mucosal route to a mammal suffering from or prone to a T-cell associated disease an immunological tolerance-inducing agent, wherein said agent comprises (i) a mucosa-binding molecule selected from the group consisting of the B subunit of cholera toxin and the B subunit of heat-labile enterotoxin of *Escherichia coli*, linked to (ii) a specific tolerogen associated with said T-cell associated immune response, and wherein said agent is administered in an amount and for a time effective to induce tolerance against said T-cell associated immune response.

2. A method as defined in claim 1, wherein said T-cell-associated immunological response is selected from the group consisting of: an autoimmune disorder, a tissue or cell graft rejection event, and a T-cell dependent inflammatory reaction or disorder.

3. A method as defined in claim 2, wherein said autoimmune disorder is selected from the group consisting of autoimmune diabetes, rheumatoid arthritis, multiple sclerosis, and uveoretinitis.

4. A method as defined in claim 3, wherein said autoimmune disorder is diabetes and said tolerogen is a pancreatic β-cell tolerogen.

5. A method as defined in claim 3, wherein said autoimmune disorder is multiple sclerosis and said tolerogen is a myelin-associated tolerogen.

6. A method as defined in claim 5, wherein said tolerogen is myelin basic protein.

7. A method as defined in claim 3, wherein said autoimmune disorder is uveoretinitis and said tolerogen is an eye-associated tolerogen.

8. A method as defined in claim 7, wherein said tolerogen is S-antigen.

9. A method as defined in claim 3, wherein said autoimmune disorder is rheumatoid arthritis and said tolerogen is a cartilage autoantigen.

10. A method as defined in claim 9, wherein said tolerogen is collagen.

11. A method as defined in claim 2, wherein said autoimmune disorder is selected from the group consisting of systemic lupus erythematosus (SLE), myasthenia gravis, and autoimmune homolytic anemia (AHA).

12. A method as defined in claim 11, wherein said autoimmune disorder is SLE and said tolerogen is DNA.

13. A method as defined in claim 11, wherein said autoimmune disorder is myasthenia gravis and said tolerogen is acetylcholine receptor.

14. A method as defined in claim 2, wherein said tolerogen is a transplantation antigen.

15. A method of inducing immunological tolerance in a mammal to diabetes, which comprises administering by a mucosal route to a mammal suffering from or prone to diabetes an immunological tolerance-inducing agent, wherein said agent comprises (i) a mucosa-binding molecule selected from the group consisting of the B subunit of cholera toxin and the B subunit of heat-labile enterotoxin of *Escherichia coli*, linked to (ii) a specific tolerogen comprising insulin, and wherein said agent is administered in an amount and for a time effective to induce tolerance against said diabetes.

16. A method of inducing immunological tolerance in a mammal to rheumatoid arthritis, which comprises administering by a mucosal route to a mammal suffering from or prone to rheumatoid arthritis an immunological tolerance-inducing agent, wherein said agent comprises (i) a mucosa-binding molecule selected from the group consisting of the B subunit of cholera toxin and the B subunit of heat-labile enterotoxin of *Escherichia coli*, linked to (ii) a specific tolerogen comprising cartilage-associated collagen, and wherein said agent is administered in an amount and for a time effective to induce tolerance against said rheumatoid arthritis.

17. An immunological tolerance-inducing agent for mucosal administration, comprising a mucosa-binding molecule linked to a specific tolerogen, wherein (i) said mucosa-binding molecule is selected from the group consisting of the B subunit of cholera toxin and the B subunit of heat-labile enterotoxin of *Escherichia coli*;

(ii) said mucosa-binding molecule confers binding of said agent to mucosal cells;

(iii) said tolerogen is an autoantigen; and (iv) said agent suppresses systemic antibody production and/or delayed-type hypersensitivity to said tolerogen.

18. An agent as defined in claim 17, wherein said autoantigen is associated with systemic autoantibody production.

19. An agent as defined in claim 17, wherein said autoantigen is associated with a delayed-type hypersensitivity reaction.

20. An agent as defined in claim 17, wherein said autoantigen is associated with an autoimmune disorder, a tissue or cell graft rejection event, or a T-cell mediated inflammatory reaction or disorder.

21. An agent as defined in claim 17, wherein said mucosa-binding molecule and said tolerogen are covalently coupled to each other.

22. An agent according to claim 17, wherein said tolerogen and said mucosa-binding molecule form a hybrid molecule which is derived from expression ex vivo of a fused gene or nucleotide sequence.

23. An agent as defined in claim 17, wherein said tolerogen is insulin.

24. An agent as defined in claim 17, wherein said tolerogen is a cartilage autoantigen.

25. An agent as defined in claim 24, wherein said tolerogen is collagen.

26. An immunological tolerance-inducing agent for suppressing autoimmune diabetes, comprising a mucosa-binding molecule linked to insulin, wherein (i) said mucosa-binding molecule is the B subunit of cholera toxin or the B subunit of heat-labile enterotoxin of *Escherichia coli* and confers binding of said agent to mucosal cells and (ii) said agent suppresses autoimmune diabetes.

27. An immunological tolerance-inducing agent for suppressing multiple sclerosis, comprising a mucosa-binding molecule linked to myelin basic protein, wherein (i) said mucosa-binding molecule is the B subunit of cholera toxin or the B subunit of heat-labile enterotoxin of *Escherichia coli* and confers binding of said agent to mucosal cells; and (ii) said agent suppresses multiple sclerosis.

* * * * *